(12) United States Patent
Jayne et al.

(10) Patent No.: US 10,406,066 B2
(45) Date of Patent: Sep. 10, 2019

(54) INTEGRATED EXTERNAL CHEST COMPRESSION AND DEFIBRILLATION DEVICES AND METHODS OF OPERATION

(75) Inventors: Cynthia Jayne, Redmond, WA (US); Ronald E. Stickney, Edmonds, WA (US); Richard C. Nova, Kirkland, WA (US); Stephen W. Radons, Snohomish, WA (US); David R. Hampton, Woodinville, WA (US); D. Craig Edwards, Fall City, WA (US); Joseph L. Sullivan, Kirkland, WA (US); Steven E. Sjoquist, Lynnwood, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 1363 days.

(21) Appl. No.: 12/372,523

(22) Filed: Feb. 17, 2009

(65) Prior Publication Data

US 2009/0149901 A1 Jun. 11, 2009

Related U.S. Application Data

(62) Division of application No. 10/652,392, filed on Aug. 29, 2003, now abandoned.
(Continued)

(51) Int. Cl.
*A61H 31/00* (2006.01)
*A61N 1/39* (2006.01)
(Continued)

(52) U.S. Cl.
CPC ......... *A61H 31/005* (2013.01); *A61H 31/006* (2013.01); *A61H 31/008* (2013.01);
(Continued)

(58) Field of Classification Search
CPC ............ A61H 2031/003; A61H 31/006; A61H 31/008; A61H 31/00
(Continued)

(56) References Cited

U.S. PATENT DOCUMENTS

| 1,193,476 A | 8/1916 | Block |
| 2,067,268 A | 1/1937 | Hans |

(Continued)

FOREIGN PATENT DOCUMENTS

| EP | 0509773 | 10/1992 |
| EP | 0623334 | 11/1994 |

(Continued)

OTHER PUBLICATIONS

U.S. Appl. No. 60/447,585, filed Feb. 14, 2003, entitled "Integrated CPR & AED Devices and Methods of Operation", by Jayne et al.
(Continued)

*Primary Examiner* — Tammie K Marlen
(74) *Attorney, Agent, or Firm* — Miller Nash Graham & Dunn LLP

(57) ABSTRACT

Integrated devices for performing external chest compression (ECC) and defibrillation on a person and methods using the devices. Integrated devices can include a backboard, at least one chest compression member operably coupled to the backboard, and a defibrillator module operably coupled to the backboard. The integrated devices can include physiological sensors, electrodes, wheels, controllers, human interface devices, cooling modules, ventilators, cameras, and voice output devices. Methods can include defibrillating, pacing, ventilating, cooling, and performing ECC in an integrated, coordinated, and/or synchronous manner using the full capabilities of the device. Some devices include controllers executing methods for automatically performing the coordinated activities utilizing the device capabilities.

37 Claims, 10 Drawing Sheets

Related U.S. Application Data

(60) Provisional application No. 60/447,585, filed on Feb. 14, 2003.

(51) Int. Cl.
    *A61F 7/10*         (2006.01)
    *A61F 7/02*         (2006.01)
    *A61M 16/00*      (2006.01)

(52) U.S. Cl.
    CPC .................. *A61N 1/39* (2013.01); *A61F 7/10* (2013.01); *A61F 2007/0233* (2013.01); *A61H 2201/0214* (2013.01); *A61H 2201/501* (2013.01); *A61H 2201/5007* (2013.01); *A61H 2201/5012* (2013.01); *A61H 2201/5048* (2013.01); *A61H 2201/5058* (2013.01); *A61H 2201/5097* (2013.01); *A61H 2230/04* (2013.01); *A61M 16/0048* (2013.01); *A61M 16/024* (2017.08); *A61M 2205/3553* (2013.01); *A61M 2205/3584* (2013.01)

(58) Field of Classification Search
    USPC ........................ 601/41, 44; 607/5, 42, 41, 44
    See application file for complete search history.

(56) References Cited

U.S. PATENT DOCUMENTS

| | | |
|---|---|---|
| 2,071,215 A | 2/1937 | Petersen |
| 2,195,744 A | 4/1940 | Emerson |
| 2,484,306 A | 10/1949 | McClain et al. |
| 3,219,031 A | 11/1965 | Rentsch, Jr. |
| 3,364,924 A | 1/1968 | Barkalow |
| 3,374,783 A | 3/1968 | Hurvitz |
| 3,425,409 A | 2/1969 | Isaacson et al. |
| 3,461,860 A | 8/1969 | Barkalow |
| 3,489,140 A | 1/1970 | Mullikin |
| 3,512,522 A | 5/1970 | Greenlee et al. |
| 3,552,390 A | 1/1971 | Muller |
| 3,644,943 A | 2/1972 | Parodi fu Leonardo et al. |
| 3,739,771 A | 6/1973 | Gaquer |
| 3,782,371 A | 1/1974 | Derouineau |
| 3,985,126 A | 10/1976 | Barkalow |
| 4,059,099 A | 11/1977 | Davis |
| 4,060,079 A * | 11/1977 | Reinhold, Jr. ........ A61H 31/008 128/204.18 |
| 4,198,963 A | 4/1980 | Barkalow et al. |
| 4,273,114 A * | 6/1981 | Barkalow ............ A61H 31/005 601/106 |
| 4,326,507 A | 4/1982 | Barkalow |
| 4,338,924 A | 7/1982 | Bloom |
| 4,349,015 A | 9/1982 | Alferness |
| 4,361,140 A | 11/1982 | Barkalow |
| 4,397,306 A | 8/1983 | Weisfeldt et al. |
| 4,424,806 A | 1/1984 | Newman et al. |
| 4,570,615 A | 2/1986 | Barkalow |
| 4,610,254 A | 9/1986 | Morgan et al. |
| 4,770,164 A | 9/1988 | Lach et al. |
| 4,819,627 A | 4/1989 | Connors |
| 4,895,173 A | 1/1990 | Brault et al. |
| 4,928,674 A | 5/1990 | Halperin et al. |
| 5,003,982 A | 4/1991 | Halperin |
| 5,014,374 A | 5/1991 | Williams |
| 5,056,505 A | 10/1991 | Warwick et al. |
| 5,098,369 A | 3/1992 | Heilman et al. |
| 5,176,135 A | 1/1993 | Fain et al. |
| 5,184,606 A | 2/1993 | Csorba |
| 5,217,010 A | 6/1993 | Tsitlik et al. |
| 5,222,478 A | 6/1993 | Scarberry et al. |
| 5,243,975 A | 9/1993 | Alferness et al. |
| 5,257,619 A | 11/1993 | Everete |
| 5,287,846 A | 2/1994 | Capjon et al. |
| 5,295,481 A | 3/1994 | Geeham |
| 5,327,887 A | 7/1994 | Nowakowski |
| 5,330,526 A * | 7/1994 | Fincke et al. .................. 607/142 |
| 5,399,148 A | 3/1995 | Waide et al. |
| 5,405,362 A | 4/1995 | Kramer et al. |
| 5,454,779 A | 10/1995 | Lurie et al. |
| 5,474,533 A | 12/1995 | Ward et al. |
| 5,487,722 A | 1/1996 | Weaver, II et al. |
| 5,490,820 A | 2/1996 | Schock et al. |
| 5,520,683 A * | 5/1996 | Subramaniam et al. ....... 606/32 |
| 5,549,659 A | 8/1996 | Johansen et al. |
| 5,557,049 A | 9/1996 | Ratner |
| 5,564,416 A | 10/1996 | Jones |
| 5,630,789 A | 5/1997 | Schock et al. |
| 5,634,222 A | 6/1997 | Zwickey |
| 5,634,886 A | 6/1997 | Bennett |
| 5,645,522 A | 7/1997 | Lurie et al. |
| 5,657,751 A | 8/1997 | Karr, Jr. |
| 5,664,563 A | 9/1997 | Schroeder et al. |
| 5,716,380 A | 2/1998 | Yerkovich et al. |
| 5,738,637 A | 4/1998 | Kelly et al. |
| 5,743,864 A | 4/1998 | Baldwin, II |
| 5,755,275 A | 5/1998 | Rose et al. |
| 5,769,800 A | 6/1998 | Gelfand et al. |
| 5,772,613 A | 6/1998 | Gelfand et al. |
| D399,000 S | 9/1998 | Rothman et al. |
| 5,806,512 A | 9/1998 | Abramov et al. |
| 5,833,711 A | 11/1998 | Schneider, Sr. |
| 5,891,062 A | 4/1999 | Schock et al. |
| 5,975,081 A * | 11/1999 | Hood ........................ A61G 1/00 128/845 |
| 5,997,488 A | 12/1999 | Gelfand et al. |
| 6,021,349 A | 2/2000 | Arand et al. |
| 6,059,750 A | 5/2000 | Fogarty et al. |
| 6,066,106 A | 5/2000 | Sherman et al. |
| 6,090,056 A | 7/2000 | Bystrom et al. |
| 6,125,299 A | 9/2000 | Groenke et al. |
| 6,142,962 A | 11/2000 | Mollenauer et al. |
| 6,149,670 A | 11/2000 | Worthen et al. |
| 6,171,267 B1 | 1/2001 | Baldwin, II |
| 6,174,295 B1 | 1/2001 | Cantrell et al. |
| 6,179,793 B1 | 1/2001 | Rothman et al. |
| 6,213,960 B1 | 4/2001 | Sherman et al. |
| 6,234,984 B1 | 5/2001 | Kelly et al. |
| 6,259,949 B1 | 7/2001 | Rosborough et al. |
| 6,263,238 B1 | 7/2001 | Brewer et al. |
| 6,277,143 B1 | 8/2001 | Klatz et al. |
| 6,312,399 B1 | 11/2001 | Lurie et al. |
| 6,325,771 B1 | 12/2001 | Kelly et al. |
| 6,334,070 B1 | 12/2001 | Nova et al. |
| 6,351,671 B1 | 2/2002 | Myklebust et al. |
| 6,374,827 B1 | 4/2002 | Bowden et al. |
| 6,390,996 B1 | 5/2002 | Halperin et al. |
| 6,398,744 B2 | 6/2002 | Bystrom et al. |
| 6,398,745 B1 | 6/2002 | Sherman et al. |
| D461,008 S | 7/2002 | Hampf et al. |
| 6,447,465 B1 | 9/2002 | Sherman et al. |
| 6,461,315 B1 | 10/2002 | Gattinoni |
| 6,533,739 B1 | 3/2003 | Palmer et al. |
| 6,568,009 B2 | 5/2003 | Linger et al. |
| 7,226,427 B2 | 6/2007 | Steen |
| 7,308,304 B2 | 12/2007 | Hampton et al. |
| 7,569,021 B2 | 8/2009 | Sebelius et al. |
| 7,775,996 B2 | 8/2010 | Stromsnes |
| 7,841,996 B2 | 11/2010 | Sebelius et al. |
| 8,002,720 B2 | 8/2011 | Hansen |
| 2001/0018562 A1 | 8/2001 | Sherman et al. |
| 2001/0011159 A1 | 9/2001 | Cantrell et al. |
| 2001/0025151 A1 | 9/2001 | Kimball et al. |
| 2001/0047140 A1 | 11/2001 | Freeman |
| 2002/0007132 A1 | 1/2002 | Rothman et al. |
| 2002/0026131 A1 | 2/2002 | Halperin |
| 2002/0026229 A1 | 2/2002 | Weil et al. |
| 2002/0032383 A1 | 3/2002 | Weil et al. |
| 2002/0055694 A1 | 5/2002 | Halperin et al. |
| 2002/0117173 A1 | 8/2002 | Lynn et al. |
| 2002/0128571 A1 | 9/2002 | Brenneman |
| 2002/0133197 A1 | 9/2002 | Snyder et al. |
| 2002/0177793 A1 | 11/2002 | Sherman et al. |
| 2002/0193848 A1 | 12/2002 | Lyster et al. |
| 2003/0055477 A1 * | 3/2003 | Dupelle et al. ................ 607/142 |

(56) References Cited

U.S. PATENT DOCUMENTS

| | | | |
|---|---|---|---|
| 2003/0088276 A1* | 5/2003 | Covey et al. | 607/5 |
| 2003/0149462 A1* | 8/2003 | White et al. | 607/142 |
| 2003/0181834 A1* | 9/2003 | Sebelius et al. | 601/41 |
| 2003/0233129 A1 | 12/2003 | Matos | |
| 2004/0082888 A1 | 4/2004 | Palazzolo et al. | |
| 2004/0158303 A1 | 8/2004 | Lennox et al. | |
| 2009/0260637 A1 | 10/2009 | Sebelius et al. | |
| 2010/0063425 A1 | 3/2010 | King et al. | |
| 2011/0308534 A1 | 12/2011 | Sebelius et al. | |

FOREIGN PATENT DOCUMENTS

| | | |
|---|---|---|
| FR | 1476518 A | 4/1967 |
| FR | 2382889 A1 | 10/1978 |
| GB | 1187274 | 4/1970 |
| SE | 521141 C2 | 10/2003 |
| WO | 96/28128 | 9/1996 |
| WO | 96/28129 | 9/1996 |
| WO | 99/36028 | 7/1999 |
| WO | 00/27336 | 5/2000 |
| WO | 00/27464 | 5/2000 |
| WO | 2012038855 | 3/2012 |

OTHER PUBLICATIONS

U.S. Appl. No. 10/652,392, filed Aug. 29, 2003, entitled "Integrated External Chest Compression and Defibrillation Devices and Methods of Operation," by Jayne et al.

U.S. Appl. No. 10/652,148, filed Aug. 29, 2003, entitled "Cooperating Defibrillators and External Chest Compression Devices," by Hampton et al.

U.S. Appl. No. 10/652,965, filed Aug. 29, 2003, entitled "Defibrillators Learning of Other Concurrent Therapy," by Nova et al.

Tsuji, et al., Development of a Cadiopulmonary Resuscitation Vest Equipped with a Defibrillator, Engineering in Medicine and Biolody Society, Proceedings of the 20th Annual International Conference of IEEE, vol. 1, 1998, pp. 426-427.

Cohen, et al., Active Compression-Decompression. A New Method of Cardiopulmonary Resuscitation, Journal of the American Medical Association, Jun. 3, 1992, vol. 267, Issue 21, pp. 2916-2923.

Steen, et al., The Critical Importance of Minimal Delay Between Chest Compressions and Subsequent Defibrillation: A Haemodynamic Explanation, Resuscitation, Sep. 2003, vol. 58, Issue 3, pp. 249-258.

Chamberlain, et al., Time for Change?, Resuscitation, 2003, vol. 58, Issue 3, pp. 237-247.

U.S. Appl. No. 10/105,054, filed Jun. 22, 2004, Non-Final Office Action.
U.S. Appl. No. 10/105,054, filed Sep. 13, 2004, Response to Non-Final Office Action.
U.S. Appl. No. 10/105,054, filed Dec. 13, 2004, Final Office Action.
U.S. Appl. No. 10/105,054, filed Mar. 16, 2005, Response to Final Office Action.
U.S. Appl. No. 10/105,054, filed Jun. 1, 2005, Non-Final Office Action.
U.S. Appl. No. 10/105,054, filed Dec. 1, 2005, Response to Non-Final Office Action.
U.S. Appl. No. 10/105,054, filed Feb. 28, 2006, Final Office Action.
U.S. Appl. No. 10/105,054, filed Aug. 28, 2006, Response to Final Office Action.
U.S. Appl. No. 10/105,054, filed Nov. 6, 2006, Final Office Action.
U.S. Appl. No. 10/105,054, filed Dec. 26, 2006, Response to Final Office Action.
U.S. Appl. No. 10/105,054, filed Mar. 5, 2007, Response to Final Office Action.
U.S. Appl. No. 10/105,054, filed May 21, 2007, Non-Final Office Action.
U.S. Appl. No. 10/105,054, filed Nov. 16, 2007, Response to Non-Final Office Action.
U.S. Appl. No. 10/105,054, filed Feb. 11, 2008, Final Office Action.
U.S. Appl. No. 10/105,054, filed Mar. 25, 2008, Response to Final Office Action.
U.S. Appl. No. 10/105,054, filed May 12, 2008, Response to Final Office Action.
U.S. Appl. No. 10/105,054, filed Jul. 30, 2008, Non-Final Office Action.
U.S. Appl. No. 10/105,054, filed Dec. 24, 2008, Response to Non-Final Office Action.
U.S. Appl. No. 10/105,054, filed Apr. 13, 2009, Final Office Action.
U.S. Appl. No. 10/105,054, filed May 6, 2009, Response to Final Office Action.
U.S. Appl. No. 13/197,667, filed May 6, 2013, Non-Final Office Action.
U.S. Appl. No. 13/197,667, filed Jun. 20, 2013, Response to Non-Final Office Action.
U.S. Appl. No. 13/197,667, filed Nov. 8, 2013, Final Office Action.
U.S. Appl. No. 13/197,667, filed Jan. 7, 2014, Response to Final Office Action.
U.S. Appl. No. 12/491,881, filed May 20, 2011, Non-Final Office Action.
U.S. Appl. No. 13/225,218, filed Apr. 25, 2013, Non-Final Office Action.
U.S. Appl. No. 13/225,218, filed Jul. 25, 2013, Response to Non-Final Office Action.
U.S. Appl. No. 13/225,218, filed Aug. 29, 2013, Final Office Action.
U.S. Appl. No. 13/225,218, filed Oct. 29, 2013, Response to Final Office Action.
U.S. Appl. No. 13/225,218, filed Nov. 20, 2013, Non-Final Office Action.
U.S. Appl. No. 13/225,218, filed Feb. 11, 2014, Response to Non-Final Office Action.
U.S. Appl. No. 13/225,218, filed Mar. 18, 2014, Final Office Action.
U.S. Appl. No. 13/419,367, filed May 3, 2013, Non-Final Office Action.
U.S. Appl. No. 13/419,367, filed Jul. 23, 2013, Response to Non-Final Office Action.
U.S. Appl. No. 13/419,367, filed Dec. 3, 2013, Final Office Action.
U.S. Appl. No. 13/419,367, filed Jan. 20, 2014, Response to Final Office Action.
U.S. Appl. No. 13/419,367, filed Mar. 3, 2014, Response to Final Office Action.
U.S. Appl. No. 13/419,367, filed Mar. 21, 2014, Non-Final Office Action.
U.S. Appl. No. 13/419,367, filed May 15, 2014, Response to Non-Final Office Action.
U.S. Appl. No. 13/419,367, filed Sep. 10, 2014, Response to Final Office Action.
U.S. Appl. No. 13/419,367, filed Oct. 15, 2014, Response to Final Office Action.
U.S. Appl. No. 13/419,367, filed Nov. 20, 2014, Non-Final Office Action.
U.S. Appl. No. 13/419,367, filed Jan. 16, 2015, Response to Non-Final Office Action.
U.S. Appl. No. 13/419,367, filed Jul. 10, 2014, Final Office Action.

* cited by examiner

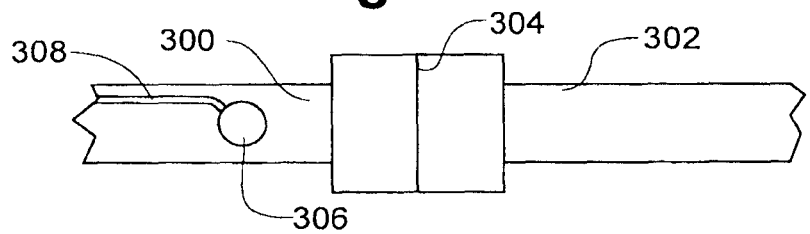
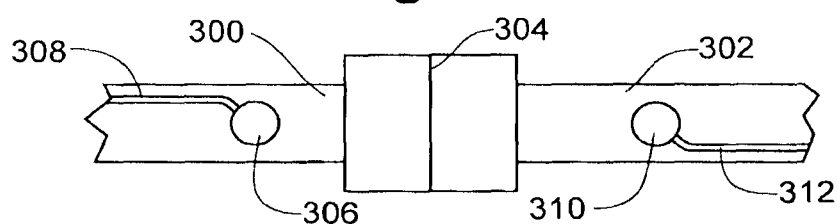
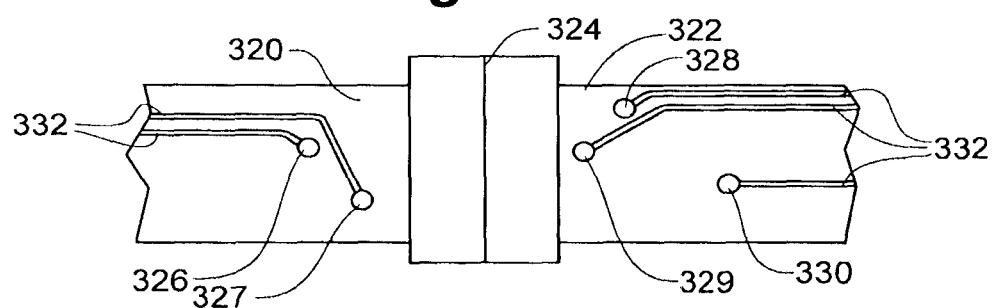
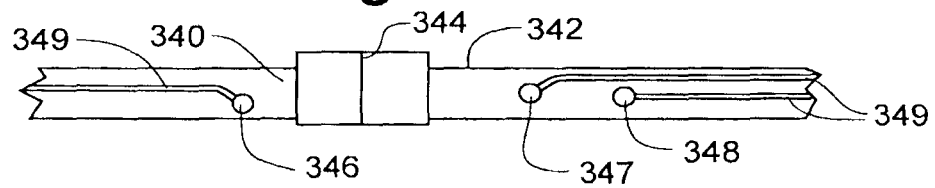

INTEGRATED EXTERNAL CHEST COMPRESSION AND DEFIBRILLATION DEVICES AND METHODS OF OPERATION

RELATED APPLICATIONS

This application is a divisional of U.S. application Ser. No. 10/652,392, filed Aug. 29, 2003, which claims the benefit of U.S. Provisional Patent Application No. 60/447,585, titled INTEGRATED CPR & AED DEVICES AND METHODS OF OPERATION, filed Feb. 14, 2003, herein incorporated by reference in its entirety. The present application is related to U.S. patent application Ser. No. 10/652,148, titled COOPERATING DEFIBRILLATORS AND EXTERNAL CHEST COMPRESSION DEVICES, filed Aug. 29, 2003, now issued as U.S. Pat. No. 7,308,304 and to U.S. patent application Ser. No. 10/652,965, titled DEFIBRILLATORS LEARNING OF OTHER CONCURRENT THERAPY, filed Aug. 29, 2003, now abandoned.

BACKGROUND OF THE INVENTION

Field of the Invention

The present invention is related to the field of resuscitation devices.

Description of the Related Art

All over the world, people experience cardiac and respiratory events. For example, both in and out of the hospital, there is a significant incidence of cardiac and/or respiratory arrest. For these situations, a variety of therapies may be appropriate. The patient may require artificial respiration, chest compressions, defibrillation, and/or pacing.

Many patents exist discussing devices related to these events and situations. For example, a chest compression device is taught in U.S. Pat. No. 6,234,984 B1. Some of these devices even aggregate such features, such as are described in U.S. Pat. Nos. 4,349,015, and 4,424,806.

Many of the prior art devices, however, merely aggregate such features, without making them work together. Therefore there exists a need for devices that can combine, coordinate and integrate various aspects of these diagnostics and therapies to better diagnose and treat the patient. That is because many of these conditions are related, and a patient might need one of these therapies alternating with another.

SUMMARY OF THE INVENTION

The present invention overcomes these problems and limitations of the prior art. Generally, the present invention provides devices, software, and methods as described below. Some embodiments of the invention provide a single device that can monitor a patient and administer diverse therapies as they arise.

In general, the preferred device of the invention includes functionalities that may perform chest compressions automatically, as well as defibrillate, monitor, pace, and ventilate. Preferably, all of these functions are automated. For those that are not automated, preferably there are instructions issued to the user.

One benefit of the invention is that monitoring and treatment are made more comprehensive, and synergies are accomplished between the disparate monitoring and treatment modes. Moreover, the invention can permit the user to carry a single item to the rescue scene.

The present invention provides an integrated device for performing external chest compression (ECC) and defibrillation on a person. The integrated device can include a backboard, at least one chest compression member operably coupled to the backboard, and a defibrillator module operably coupled to the backboard. Some devices include at least one sensor for outputting data and sensing physiological data from the patient. The backboard can be formed of an electrically non-conductive material and can have an electrode disposed in the backboard. In some devices, the physiological data includes at least one attribute from the group consisting of pulse, heart beat, breathing, body temperature, externally applied chest pressure, and thoracic impedance. Some devices include wheels and a handle for transporting the device and/or transporting a patient on the device. A controller or processor may be coupled to the device and may be further coupled to a human interface module or I/O module. The controller can be coupled to the sensor and can execute logic to defibrillate the person responsive to sensor data indicative of cardiac arrest. In some embodiments, the controller can execute logic to pace the person responsive to sensor data indicative of bradycardia.

Some devices include a cooling module for cooling the person. The cooling module can include a cooling garment that can be placed over the person. In some devices, a controller can execute logic to initiate cooling responsive to sensor data indicative of cardiac arrest in the person.

Devices can include an electrode attached to the chest compression member of the device. Some electrodes include a releasable electrolyte that can be released upon application of pressure or an external signal. Chest compression members can include a belt and/or a vest, which can be coupled to a powered actuator for retracting the belt or vest. Some chest compression members include a rigid member pivotally coupled to the backboard. The rigid member can be coupled to a powered actuator for effecting ECC, or may be manually operable, depending on the embodiment. Some chest compression members include a pressure sensor for measuring external pressure applied to the chest. Other devices include a second defibrillation electrode, where the second defibrillation electrode can be disposed on the belt, vest, or other chest compression member. Some devices include multiple defibrillation electrodes coupled to the chest compression member. Multiple ECG electrodes may also be disposed on the belt, vest, or other chest compression member.

A voice output device may be included in some integrated devices. A camera coupled to a transmitter may be included in other devices. A ventilator for ventilating the patient can be included in still other integrated devices according to the present invention.

One method according to the present invention includes placing a person on a backboard of an integrated device, causing a chest compression member of the device to compress the person's chest against the backboard, causing the device to sense physiological signals of the person by a sensor, and causing a defibrillation module of the device to defibrillate the person depending on the sensed signals or responsive to the signals. Some methods further include listening to a voice output of the device. The signals can be sensed by bringing the sensor in contact with the person in some methods. The sensors may be brought in contact with the person by bringing the chest compression member in contact with the chest. Placing the person on the backboard can result in the person contacting a defibrillator electrode of the device.

Some methods include cooling the person using a cooling module of the device, which can include a cooling garment, or the cooling can be performed responsive to physiological signals of the person. The cooling may be performed automatically by the integrator device responsive to the physiological signals. Some methods include ventilating the person using a ventilator of the device, or the ventilating can be performed responsive to the physiological signals. In still other methods, the person is paced using a pacing module of the device, to pace the person responsive to the signals.

The present invention also includes methods that can be implemented using a controller or processor of the integrated device. The methods can be implemented using hardware, software, firmware, or other modality. The methods implemented in any of these modalities can reside in a computer-readable media.

One method that can be implemented in a controller includes receiving an input that a person has been placed on a device backboard and generating instructions to operate a chest compression member of the device to compress the person against the backboard. The method can further include receiving a physiological signal of the person and operating a defibrillation module of the device to defibrillate the person in response to the signal. The chest compression member can also be controlled in response to the signal. Some methods can generate voice outputs that can issue chest compression instructions, drug delivery instructions, manual ventilation instructions, cooling instructions, precordial thump delivery instructions, and/or instructions to manually ventilate the person in synchrony with the chest compression instructions.

Some methods generate instructions to initiate defibrillation responsive to physiological signals indicative of ventricular fibrillation, ventricular tachycardia, and/or other physiological signals indicative of cardiac arrest. Methods can include generating instructions to ventilate the person in response to physiological signals indicative of lack of breathing. Some methods generate instructions to operate a pacing module responsive to physiological signals indicative of ventricular bradycardia. Instructions may also be generated to monitor thoracic impedance over time. Methods may include monitoring chest compressions and generating instructions to operate a pacing module in synchrony with the monitored chest compressions.

DESCRIPTION OF THE DRAWINGS

FIG. 8 is a fragmentary, bottom view of a belt bearing a defibrillator electrode;

FIG. 9 is a fragmentary, bottom view of a belt bearing two defibrillator electrodes;

FIG. 10 is a fragmentary, bottom view of a belt bearing multiple ECG leads;

FIG. 11 is a fragmentary, bottom view of a belt bearing multiple sensors and associated leads;

DETAILED DESCRIPTION

Figure 1:
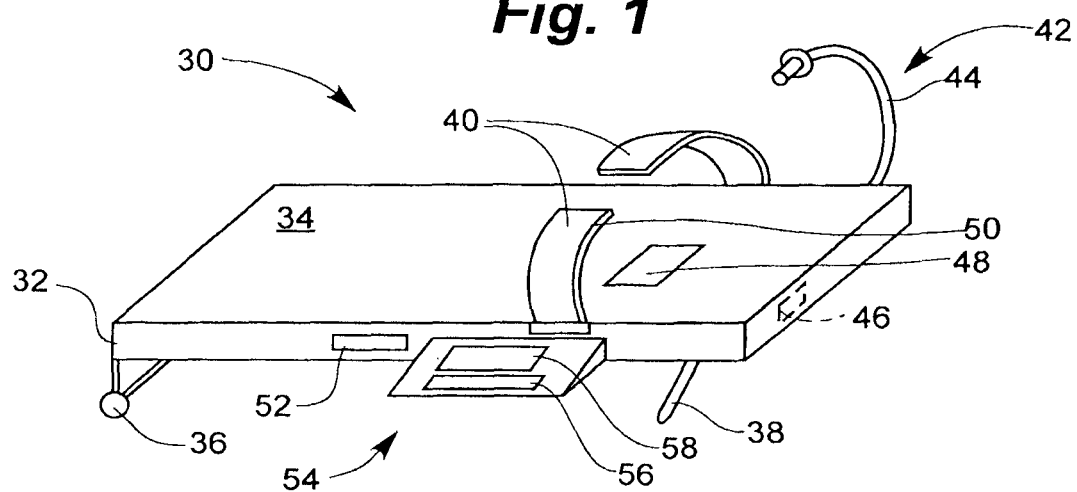
FIG. 1 is a perspective view of an integrated external chest compression (ECC) and defibrillation device.

FIG. 1 illustrates an integrated external chest compression (ECC) and defibrillation device 30. Integrated device 30 includes a backboard or back frame 32, chest compression members 40, a ventilator 42, a human interface device 54, and a defibrillating and/or pacing module 46.

Backboard 32 is shown as solid and having an upper surface 34. Backboard 32 need not be solid. Backboard 32 is preferably made as lightweight as possible, allowing the integrated modules to be included without adding unneeded weight. In some embodiments, wheels 36 and a handle 38 are coupled to backboard 32. This permits the device to be used as a gurney, making it easier to transport the patient.

The chest compression portion may be implemented in a number of ways, as described below. Two chest compression members 40 are shown, in the form of two arms. Chest compression members 40 are coupled to backboard 32. Even though only two arms are shown, the chest compression members may be implemented as a belt, and/or as a vest, either a full or partial vest. The belt or vest is intended to generally wrap around the chest of the patient, for squeezing it, or squeezing it against backboard 32. In this way, ECC or CPR can be administered to the patient. The belt or vest may incorporate other functionalities, as further described below. In addition, it may be removable and/or reusable.

Integrated device 30 includes a defibrillating and/or pacing module 46, hereinafter referred to generally as a defibrillating module or defibrillator. Defibrillator 46 can be electrically coupled to a posterior electrode 48 embedded in backboard 32. Backboard 32 may be formed of an electrically insulating material to electrically isolate posterior electrode 48. Electrode 48 can be disposed to contact the patient's back, on the left side. Defibrillator 46 can also be coupled to a defibrillator or pacing electrode 50, disposed on chest compression member 40. In some embodiments, at least one defibrillator electrode is disposed on the under-side of the belt, chest compression member, or vest to contact the patient's chest near the heart.

Integrated device 30 further includes a ventilator or ventilating module 42. Ventilator 42 can include ventilator tubing 44. Ventilator 42 can also be coupled to backboard 32 and can be used for ventilating the patient. Ventilator 42 is shown schematically, as ventilators are well known to those skilled in the art.

Human interface device 54 can be implemented in a number of ways. Human interface device 54 can include an input portion 56 and an output portion 58. Input portion 56 can include a keyboard and output portion 58 can include a visual display or computer screen and/or a voice output module for interacting with a human assistant. A battery 52 can be carried within backboard 32 for supplying power for operating human interface device 54, defibrillator 46, ventilator 42, and chest compression members 40, in the various embodiments of the invention. A controller or computer can also be included within human interface device 54 or elsewhere within integrated device 30 for integrating and coordinating the operation of external chest compression, defibrillating, pacing, and ventilating, depending on the embodiment of the invention present.

Figure 2:
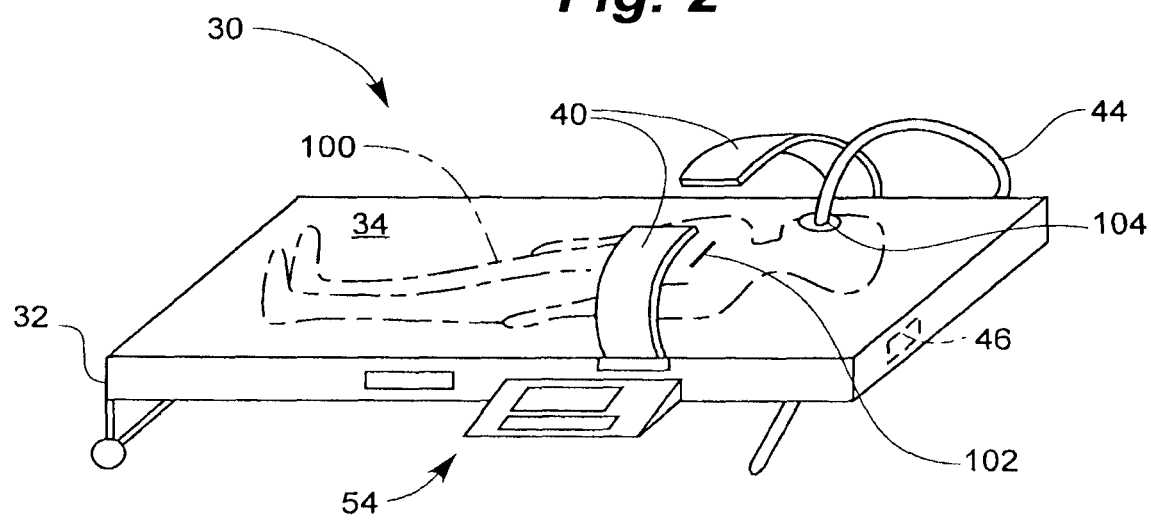
FIG. 2 is a perspective view of the integrated device of FIG. 1, having a person disposed on the device.

FIG. 2 illustrates integrated device 30 having a person or patient 100 disposed on backboard 32. Patient 100 has a chest 102 disposed under chest compression members 40 and a mouth 104 for receiving ventilator tubing 44.

Figure 3:
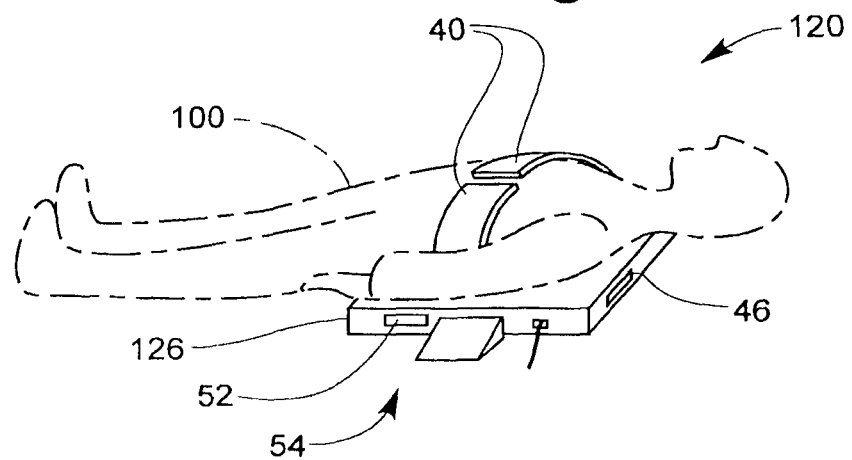
FIG. 3 is a perspective view of a person disposed on another integrated device, having a shorter backboard relative to the device of FIG. 1.

FIG. 3 illustrates another integrated device 120 for integrating external chest compression and defibrillation and/or pacing. Integrated device 120 may be seen to include chest compression members 40, human interface device 54, battery 52, and defibrillator module 46, as previously described with respect to FIG. 1. Integrated device 120 includes a short backboard or back frame 126. Shorter backboard 126 can decrease the weight and increase the portability of the integrated device.

Figure 4:
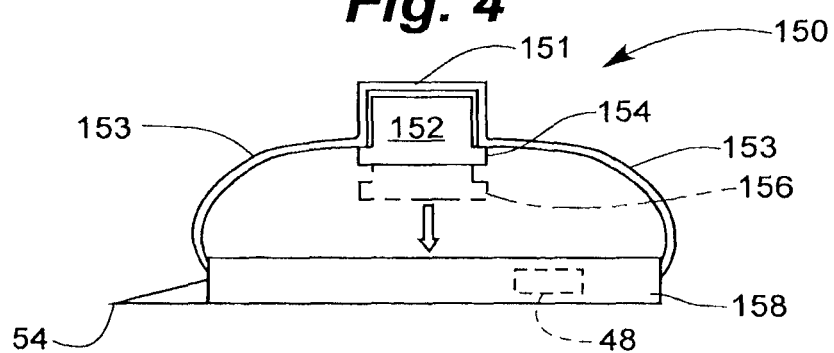
FIG. 4 is a transverse, cross-sectional view of an integrated device in which the chest compression member includes a belt and a piston.

FIG. 4 illustrates an integrated device 150, in which the chest compression is effected by a compressor or expandable member held in place by a belt or vest 153, depending on what is provided in the particular embodiment. The chest compressor includes a mechanism for pushing downwards on the chest. In the integrated device illustrated, the compressor is implemented as a base 151 and a piston 152. Piston 152 is illustrated in a first, retracted position 154 and a second, extended position 156. Belt or vest 153 can be coupled to a back frame 158, as previously discussed.

Figure 5:
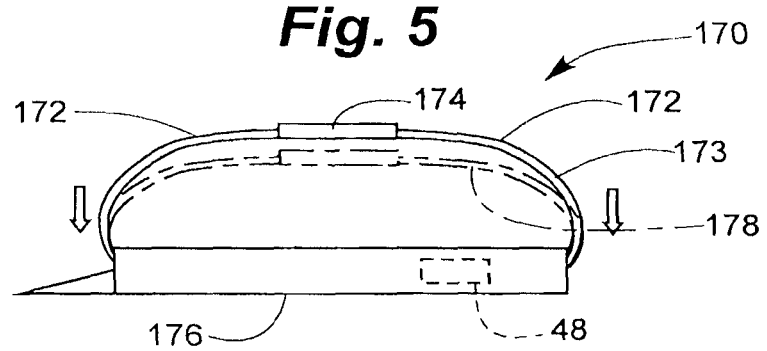
FIG. 5 is a transverse, cross-sectional view of an integrated device in which the chest compression member includes a retractable belt.

FIG. 5 illustrates an integrated device 170. The integrated device 170 includes a belt or vest 172, having a buckle, hook and loop fastener (e.g. Velcro™) or zipper 174 for fastening around the chest of the patient. Belt or vest 172 can itself be contracted to effect chest compression. The contraction can take place in many ways. In one way, the belt or vest can be retracted into a back frame 176. In another way, belt or vest 172 can be constricted about the patient. Belt or vest 172 may be seen having a first, expanded position 173 and a second, constricted position 178. In yet another way, chest compression is effected by electrically stimulating the chest muscles.

Figure 6:
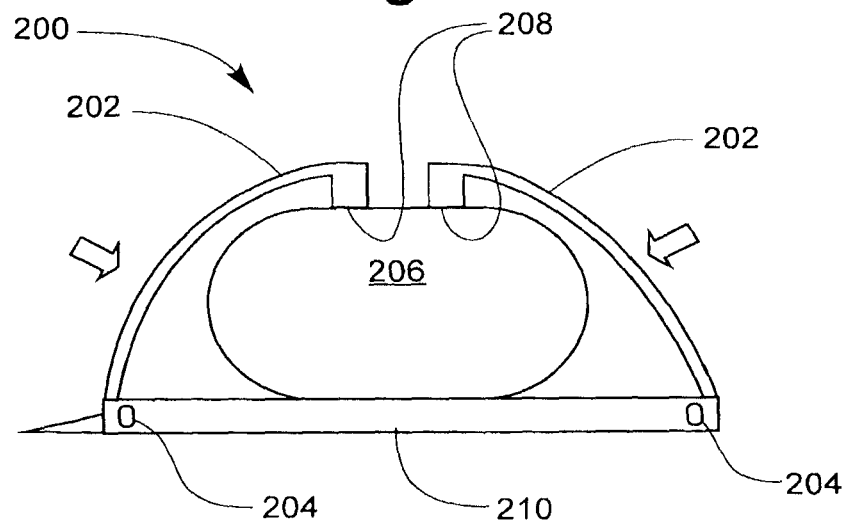
FIG. 6 is a transverse, cross-sectional view of an integrated device in which the chest compression member includes rigid members pivotally coupled to the backboard.

FIG. 6 illustrates still another integrated device 200 having a patient 206 disposed on a backboard 210. In device 200, chest compression is provided by rigid chest compression members or arms 202 having support prongs 208 that push down on the chest of patient 206. Arms 202 can be pivotally coupled to backboard 210. In the embodiment illustrated, arms 202 are operated by gears 204 that are integrated with backboard 210. In some embodiments, arms 202 are driven by a powered chest compression actuator.

Figure 7:
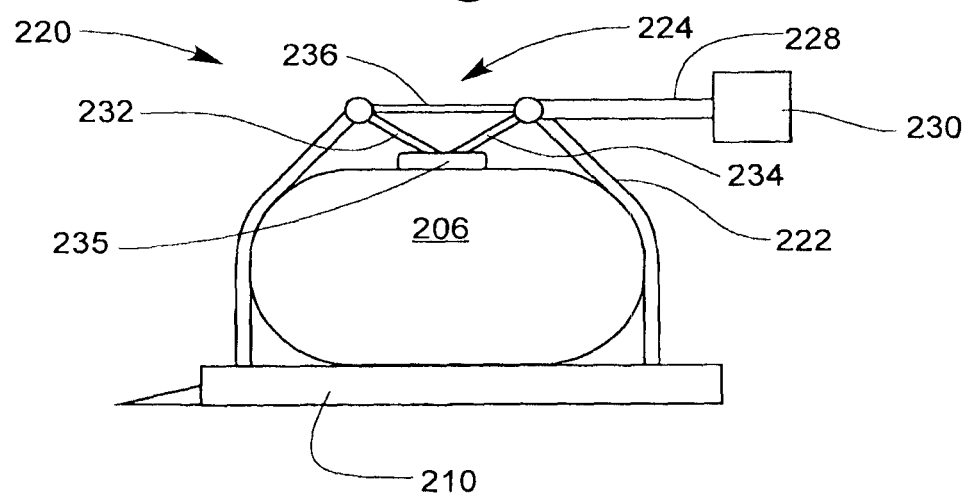
FIG. 7 is a transverse, cross-sectional view of an integrated device having a powered actuator coupled to a force multiplier for delivering chest compression.

FIG. 7 illustrates another integrated device 220 including backboard 210 carrying patient 206, as previously described. Integrated device 220 includes a force multiplier 224 using a lever arrangement, so that a pressing member can exert a downward pressure on the patient chest. Integrated device 220 includes a gear box or a powered actuator 230 coupled through a shaft or rod 228, which may be hollow in some embodiments. Shaft 228 can have first force transmission member 236 slidably received within shaft 228 and pivotally coupled to a second force transmission member 232 and a third force transmission member 234. Force transmission members 232 and 234 can be further coupled to a chest compression pad 235 for pressing against the chest of patient 206. Force multiplier device 224 can be held in place by a belt or vest 222. In some embodiments, the lever arrangement may operate by having a rod conduct a long rotation, such as in a corkscrew arrangement.

Other embodiments of the chest compression portion include belts crossing the chest from over the shoulder down to the chest, forming an "X" across the patient's chest. This is better than the conventional way of having belts horizontally across the patient's chest, in that it permits placement of sensors such as leads in different places. Alternately, an "X"-belt configuration may be combined with the conventional configuration. In yet other embodiments, the chest compression portion includes devices performing active compression-decompression, devices that combine chest compressions with abdominal compressions, devices where the belt is operated electronically without gears, and devices that use electricity to do chest compressions by electrically inducing chest muscles to contract. Various embodiments may use combinations of these chest compression techniques.

Figure 19:
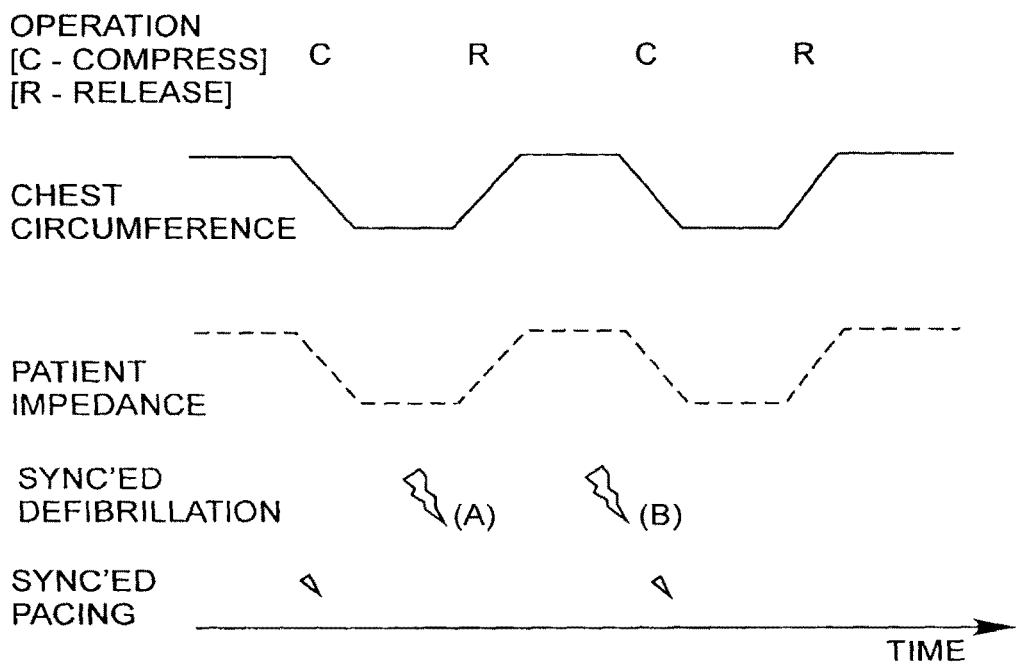
FIG. 19 is a time diagram showing coordinated periodic chest compressions and defibrillation and/or pacing pulses.

Compressing and releasing may be performed according to any type of time profile. One such profile is seen in FIG. 19. Other profiles may be sine-wave, triangular shaped, or other shapes. In an advantageous embodiment of the invention, a sine-wave may be used with a frequency outside the ECG range. This permits analyzing the ECG while simultaneously performing chest compressions. This permits the device to detect more quickly a rhythm that requires a defibrillation shock, and to reduce the delay of its delivery from the end of the chest compressions.

Referring again to FIGS. 1, 2, and 3, the invention defibrillation-pacing portion can be either formed integrally with the backboard or is removable from it. In any event, the defibrillation-pacing portion can operate when integrally connected with the back frame or backboard.

The defibrillation-pacing portion is capable of performing defibrillation, and optionally, also pacing. Pacing may be implemented by a separate module than defibrillating, but it is highly advantageous to have the same module perform both functions. The defibrillation/pacing portion may operate as a defibrillator of any chosen automation level. That includes operation that is fully automated to fully manual, and every option in between.

Moreover, the invention may also advantageously provide devices or modules that perform monitoring, and further provide interpretation of the monitored signals. The monitoring results may advantageously be displayed on the human interface device previously described or on an I/O module as described below. In other embodiments, there is a separate monitoring module. Monitoring may be of any of the monitoring parameters or physiological attributes common on defibrillator/monitors or bedside monitors today, for example, NIBP, $SpO_2$, $CO_2$, 12 lead ECG, etc. The devices that perform the monitoring are preferably integrated with the back frame, and preferably are removable for servicing.

The invention also can include an input/output (I/O) or human interface module as previously described. In the embodiment of FIG. 1, human interface device 54 includes a display screen and keyboard, as previously discussed, but that is not limiting. The invention can also have input devices such as keys, switches, knobs, levers, a microphone for voice recording, and preferably also voice recognition, and output devices such as one or more screens, a speaker, printer, or other output device. All of these are preferably aggregated at the I/O module, but that is not necessary for practicing the invention. They may be located elsewhere in the devices, or received remotely, for example, wirelessly, or transmitted wirelessly to a remote output device.

The invention also optionally includes a ventilation portion. A ventilation portion or ventilating module 42 was previously described with respect to FIG. 1. The ventilation portion may be implemented either automatically, or be intended for use by a human operator. If by a human, the device may be made giving prompts for instructing the rescuer. The prompts may be timed. The rescuer may be either performing mouth-to-mouth resuscitation or opening a bag valve mask device where the user manually squeezes the bag. If the ventilator is to be automatic, a tube can be inserted into the patient's mouth, and a pump can be used. Alternatively, a mask may be placed on the face of the patient. The oxygen can be delivered this way to the patient. Other devices, such as valves that block the airway during chest decompression, for example, the CPR-x valve, can be included in the ventilation portion of the device of the invention. To the extent it is automatic, a pump of the ventilation portion may be advantageously integrated with the back frame.

The invention preferably also includes an electrical power source for powering the various portions. The power source may be a battery, such as battery 52 discussed with respect to FIG. 1. The battery may be either a rechargeable battery for maximum portability, or a replaceable battery. The battery is preferably integrated with the back frame, either permanently, or in such a way that it can be removed and replaced. Some devices of the invention have the benefits of being able to share a common power source, CPU or controller, and I/O module for the interface with the rescuer.

FIGS. 8 and 9 illustrate how defibrillator electrodes or other electrodes might be attached to an underside of the vest or belt of the chest compression portion of the devices of FIG. 1, 2, or 3. For example, the electrodes can be part of a belt or vest of FIG. 4 or 5. The electrodes can also be integrated with an arm or a prong of a chest compression member, for example, prong 208 of FIG. 6 or chest contact pad 235 or FIG. 7.

FIG. 8 illustrates a belt or vest having a first portion 300 coupled through a buckle or zipper 304 to a second portion 302. A first electrode 306 may be affixed to the underside of the belt or vest and coupled to a wire or lead 308. In FIG. 8, one of the electrodes is situated on the underside of the belt or vest, while the other electrode may be expected to be in the backboard. At least one wire can connect the electrode to the remainder of the defibrillation/pacing portion. This is a preferred embodiment, since it would minimize CPR artifact in the ECG signal. The electrode preferably avoids the center of the chest. That is where the buckle or zipper is shown (as wider than the open portion that supports the electrode).

FIG. 9 illustrates the belt or vest of FIG. 8, having belt or vest first portion 300, buckle or zipper 304, and second portion 302. First electrode 306 and wire 308 are as previously described with respect to FIG. 8. In FIG. 9, a second electrode 310 is coupled to a second wire or lead 312. In the embodiment illustrated in FIG. 9, no electrode is needed in the backboard or back frame for traditional defibrillation. At least one wire can connect each electrode to the defibrillation/pacing portion.

FIG. 10 illustrates the underside of another belt or vest having a first portion 320 coupled through a buckle or zipper 324 to a second portion 322. Belt or vest first portion 320 may be seen carrying a first electrode 326 and a second electrode 327, coupled to wires 332. Belt or vest second portion 322 may be seen carrying third electrode 328, fourth electrode 329, and fifth electrode 330, all coupled to wires 332. Wires 332, while having similar reference numbers, are, of course, preferably electrically distinct. The ECG leads of FIG. 10 are also preferably integrated with the underside of the vest or belt of the chest compression portion of the devices of FIG. 1, 2, or 3. The ECG leads may be placed so as to not interfere with any defibrillation electrodes, for example, those of FIGS. 8 and 9.

FIG. 11 illustrates yet another belt or vest having a first portion 340 coupled through a buckle or zipper 344 to a second portion 342. The underside of belt or vest first portion 340 may be seen carrying a first sensor 346 coupled to a wire or other signal transmission medium 349. The underside of belt or vest second portion 342 may be seen carrying a second sensor 347, and a third sensor 348, coupled to wires 349. The sensors are preferably also integrated with the underside of the vest or belt of the chest compression portion of the devices of FIGS. 1, 2 and 3. These sensors can include pulse detection sensors, such as those made from piezoelectric materials, temperature sensors, $CO_2$ sensors, and other sensors for measuring physiological attributes or signals, well known to those skilled in the art.

The features integrated with the belt or vest are preferably arranged so that they do not interfere with each other. The electrode may be fully integrated, or detachable for servicing. Alternately and equivalently, some electrodes, ECG leads, or sensors may be hosted in the backboard.

Figure 12:
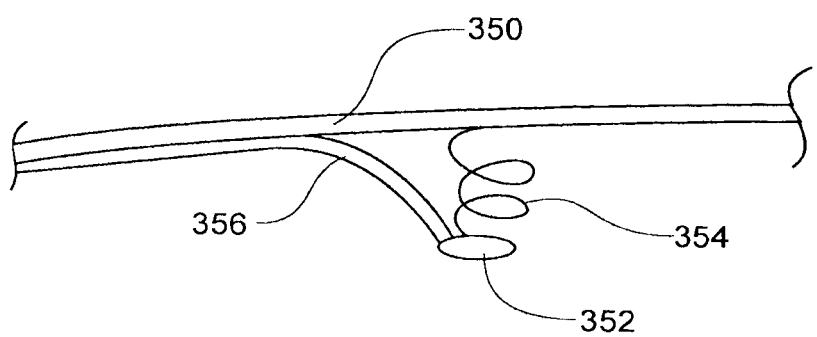
FIG. 12 is a fragmentary, transverse cross-sectional view of a belt or vest bearing a spring biased defibrillator electrode, ECG lead, or sensor.
Figure 13:
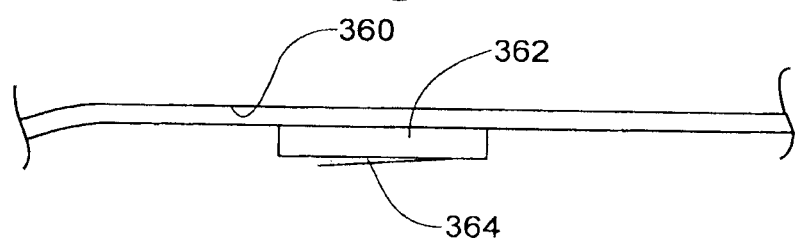
FIG. 13 is a fragmentary, transverse cross-sectional view of a belt or vest bearing an electrode, lead, or sensor having an electrolyte gel.

FIGS. 12 and 13 illustrate how defibrillator electrodes, ECG leads, or sensors may be integrated with an underside of the vest, belt, or other chest compression members, for example those in FIG. 1, 2 or 3.

FIG. 12 illustrates a belt or vest 350 carrying an electrode, lead, or sensor 352. Electrode, lead, or sensor 352 can be coupled to a wire 356 and biased downward from the belt or vest with a spring 354, so as to be pressed against the chest of the patient. For use with a pulse sensor, some quieting time for the spring is preferably allowed, so as to not provide interference with the signal.

FIG. 13 illustrates a belt or vest 360 carrying an electrode, lead, or sensor 362 on the underside of the vest or belt. A gel or electrolyte 364 may be seen on the underside of the electrode, lead, or sensor 362. For implementing an electrode, a gel may be administered, or an electrolyte may be diffused. The gel or electrolyte may be provided in a capsule that bursts at an appropriate time to release it. The time may be prior to defibrillation electrotherapy. Bursting may be caused by the mere pressure against the chest, or by an appropriate electrical signal. One advantage that can be provided by some embodiments is that there is no need to disrobe the patient—the fluid may seep through the clothes to establish electrical conduction.

Figure 14:
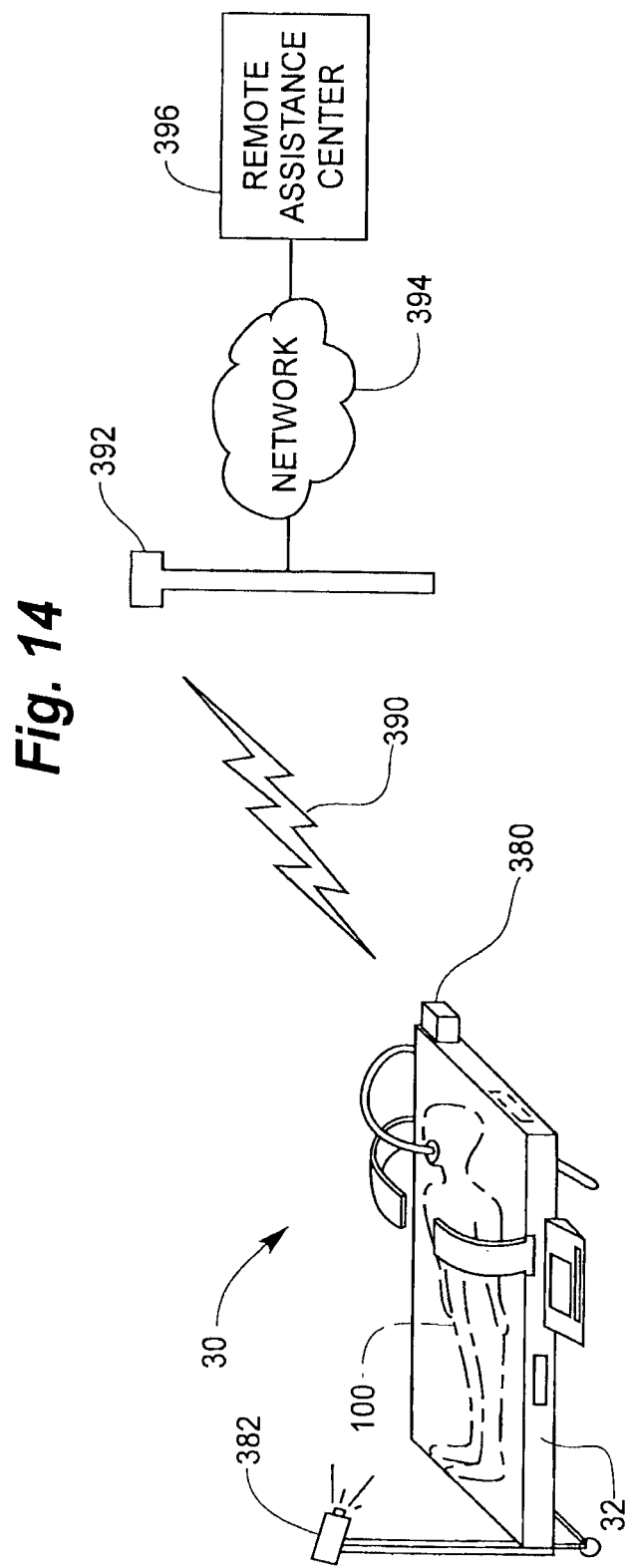
FIG. 14 is a schematic view of the integrated device of FIG. 1 further including a camera and transmitter communicating with a remote assistance center.

FIG. 14 illustrates some other optional features of the invention. Integrated device 30, patient 100, and backboard 32 are shown, as previously described. A camera 382 may be seen disposed on a post secured to backboard 32. Camera 382 can be coupled to a communication module 380 that can act as a transmitter or transceiver. Communication module 380 can communicate with a remote assistance center 396 coupled through a network 394 and a remote antenna 392. A data/voice/video communications link 390 is shown as existing between communication module 380 and remote assistance center antenna 392. Communication link 390 can be bi-directional in some embodiments. In a preferred embodiment, communications module 380 includes the functionality of a portable telephone, and network 394 is a network that can support voice and/or data communications. Camera 382 is preferably a digital camera, and may be either a video camera or a still camera. The camera may be advantageously attached to a post in the backboard. This permits recording of the scene and the patient. The recording may be used for record keeping, event analysis, and other purposes. Alternately, the recording may be used for live transmission to the remote assistance center 396, where more trained medical personnel can in turn provide feedback.

The user of the invention can establish communication link 390 with remote assistance center 396. Then the information can be transmitted and can include images, if a camera is provided. The patient's vital signs, encoded by the invention for communication, along with the rescuer's comments, observations, and even questions may be also transmitted to the remote assistance center.

In some embodiments, the invention is operable from remote assistance center 396. An operator at the remove assistance center can transmit a command code through communication link 392 integrated device 30, and integrated device 30 operated accordingly. Such operation may actually include defibrillation.

Moreover, the monitored data, included also recorded data such as events, wave forms, physiological signals or attributes, and data indicative of the device operation itself, may be also transmitted to a system for collecting or storing patient information, and to a computer-aided dispatch system for assistance. Furthermore, it may also be sent to a billing system for determining patient billing.

Figure 15:
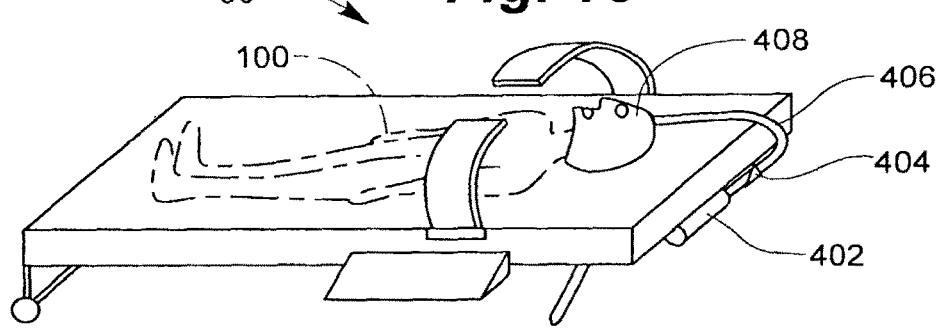
FIG. 15 is a schematic view of the integrated device of FIG. 1, further including a cooling module in the form of a cooling garment disposed on the person.
Figure 16:
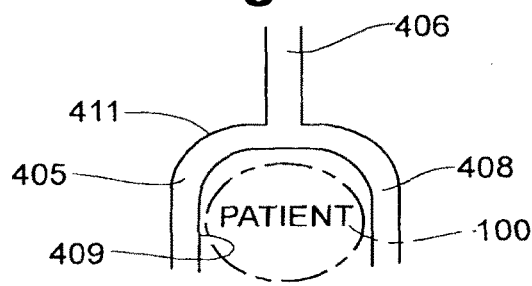
FIG. 16 is a highly diagrammatic, cross-sectional view of the person and cooling garment of FIG. 15.

FIGS. 15 and 16 illustrate additional optional cooling figures of the invention. Cooling can be provided for performing IMHT (Induction of Mild Hypo Thermia), which may slow down adverse effects of the events being experienced by the patient.

Integrated device 30 and patient 100 are as previously described. FIG. 15 illustrates generally a cooling module aspect of the present invention. In the example illustrated, the cooling module includes a liquid gas storage container or tank 402 coupled to a valve 404 coupled in turn to a tube 406 coupled to a cooling garment 408. Liquid gas storage container 402 can be included within the cooling module and is preferably carried under the backboard. This is most advantageous in the event the backboard is implemented with wheels.

The liquid in container 402 can be one that preferably turns into gas upon being released into the atmosphere. A cooling garment, similar to cooling garment 408, can be provided for each part of the body that is of interest to cool. The cooling garment can be shaped to be suitable for placing over the bodily part that is to be cooled. Cooling garment 408 illustrated in FIG. 15 is designed for placement on the patient's head. Cooling may also be accomplished by evaporative cooling, for example, using a suitable fluid delivery system and an absorber for alcohol, such as cotton.

FIG. 16 illustrates a section of cooling garment 408. Garment 408 has an inner shell 409 for contacting patient 100. Garment 408 also has an outer garment or shell 411 that defines an inner space 405 between outer shell 411 and inner shell 409. Spacers may be used to maintain inner space 405 in an open configuration. Alternately, small tubes may be used. Garment 408 can receive liquid gas from storage container 402 via tube 406 in communication with inner space 405. The cooling gas or liquid can also be received into the series of small tubes, previously described. The gas can then be released into the atmosphere from various places in the garment. As it is being released, the gas can expand, cool, and thus draw heat away from the patient. Sensors, for example for temperature, may also be included.

Referring again to FIG. 15, the gas can be directed from storage container 402 to liquid controller or valve 404, and from there to garment 408 via tube 406. Liquid controller 404 can in turn be controlled by an IMHT controller, for controlling the rate of cooling of the patient. The expanded cooled gas may be mixed with air to control the final cooling gas/air temperature. The IMHT controller may be implemented in combination with the liquid controller, and optionally further communicates with the processor or controller of the device of the invention.

The present invention may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented as an Application Specific Integrated Circuit (ASIC), etc. These features can be integrated with the invention, or coupled with it.

Moreover, the invention additionally provides methods, which are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between the method of the invention itself and the method of operating a computing machine. The present invention relates both to methods in general, and also to steps for operating a computer and for processing electrical or other physical signals to generate other desired physical signals.

The invention additionally provides programs, and methods of operation of the programs. A program is generally defined as a group of steps leading to a desired result, due to their nature and their sequence. A program made according to an embodiment of the invention is most advantageously implemented as a program for a computing machine, such as a general-purpose computer, a special purpose computer, a microprocessor, etc.

The invention also provides storage media that, individually or in combination with others, have stored thereon instructions of a program made according to the invention. A storage medium according to the invention is a computer-readable medium, such as a memory, and is read by the computing machine mentioned above.

The steps or instructions of a program made according to an embodiment of the invention requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

Figure 17:
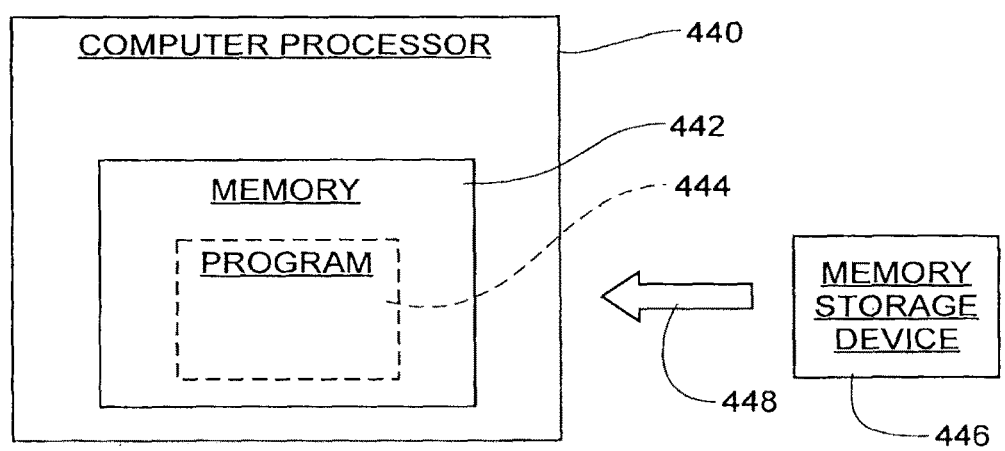
FIG. 17 is a block diagram of the controller or computer containing executable logic or software contained within an integrated device.

FIG. 17 illustrates a general computer, processor, or controller 440 having a data storage device or computer readable medium 446 interfaced with computer 440 to transfer data via link 448, or the data may define a program. Computer 440 of FIG. 17 may be implemented by a CPU, and preferably interfaces with the IO module or human interface device previously described. Computer or controller 440 includes a memory 442 containing executable logic or program 444.

This detailed description portion is presented largely in terms of flowcharts, display images, algorithms, and symbolic representations of operations of data bits within at least one computer readable medium, such as a memory. An economy is achieved in the present document in that a single set of flowcharts is used to describe both methods of the invention, and programs according to the invention. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software and softwares. This is not necessary, however, and there may be cases where modules are equivalently aggregated into a single program with unclear boundaries. In any event, the software modules or features of the present invention may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps which may be performed by different modules of an overall parts of a software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

In the present case, methods of the invention are implemented by machine operations. In other words, embodiments of programs of the invention are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods of the invention are now described.

Figure 18:
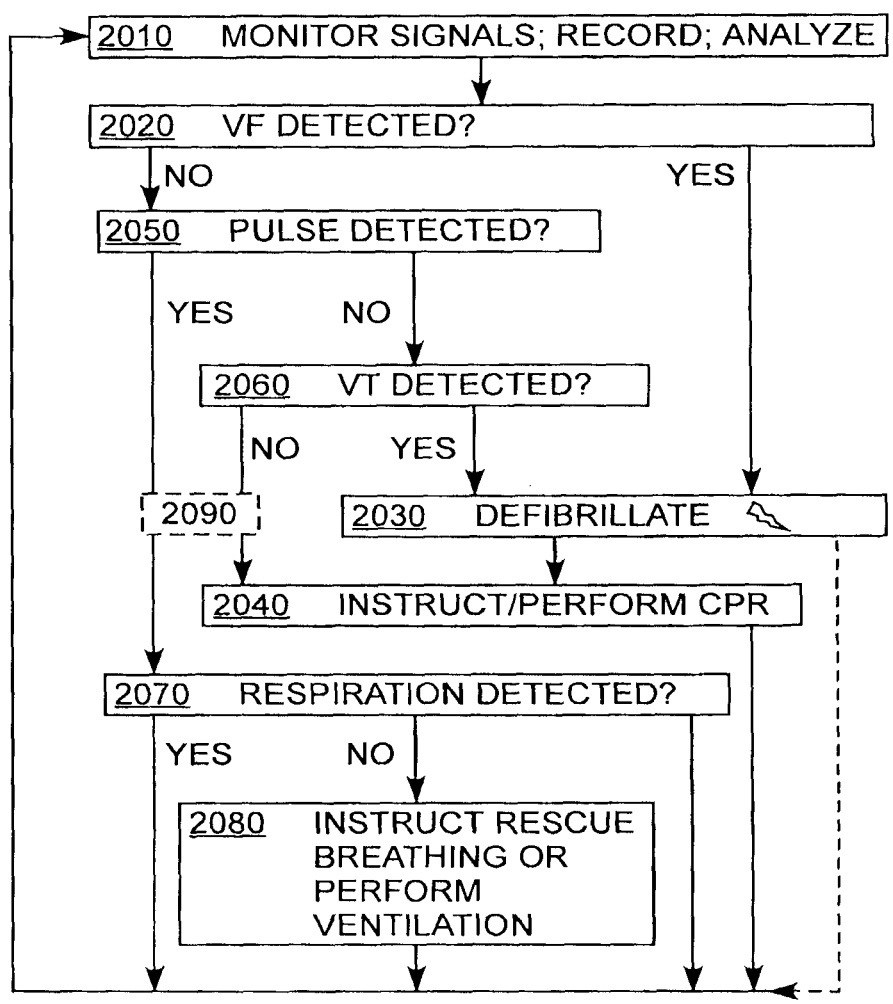
FIG. 18 is a flow chart illustrating a method for integrating external chest compression and defibrillation therapies.

Referring now to FIG. 18, a flowchart 2000 is used to illustrate a method according to an embodiment of the invention. The method of flowchart 2000 may also be practiced by the devices of the invention described in this document. Above and beyond the method described herein, the responder (who is also a user) may be instructed on how to apply a device, and or interactively give feedback, and/or to perform steps of the method, etc.

According to a box 2010, signals are received about the patient, and optionally are also monitored. Optionally, they are also recorded, displayed, transmitted, etc.

The signals are received from the patient (such as ECG), from special sensors (such as oximetry, impedance, force, pulse detection sensors, etc.). Signals may also be received from other components or devices (size of belt or vest around patient's chest, GPS signals, control signals from a device of a responder attending to the patient, etc.). Signals may further be received from the responder interactively, e.g. by asking questions and receiving answers.

The signals are then analyzed and treated as inputs, as is also shown in the rest of flowchart 2000. Analysis may be implemented also by taking advantage of the combined functionalities and features. For example, knowledge of the time profile of the chest compression is used to remove the chest compression artifact from the ECG.

The process of box 2010 preferably takes place continuously, even if execution moves also to other boxes of flowchart 2000. Monitoring is for the conditions that are applicable for the below, including, for example, for the effectiveness of chest compressions. There can be different stages of monitoring, such as main monitoring, at exact box 2010, and secondary monitoring concurrent with other stages, e.g. at the same time as any one of boxes 2030, 2040, 2080 below.

In addition, monitoring may be also for detecting Acute Myocardial Infarction (AMI), via the ECG or other monitoring parameters, and indicating this to the caregiver. If AMI is detected, then monitoring may also be for cardiac arrest (which commonly occurs following an AMI).

In addition to monitoring, preferably there is also recording. The accumulated record may include records of events, data monitored, and functionalities of the invention that are operating, and time profiles of their operation.

A number of decision trees may then be implemented, in determining what action to take next. The best embodiments known to the inventors are described, but that is only by way of example, and not of limitation. Further, the flowchart may be integrated with other steps, such as administering medications (e.g. cardiac drugs), etc. But simplistically, the ECG input is analyzed for a shockable rhythm, and then either defibrillation takes place, or pulse or other signs of circulation are checked, following the same protocol as today's AEDs. Further, a user would be prompted to start the CHEST COMPRESSION PORTION device and ventilations if there was no pulse (or no signs of circulation). A more rigorous way is described below.

According to a next box 2020, it is determined whether Ventricular Fibrillation (VF) of the patient's heart is occurring. If so, then according to a next box 2030, the patient is defibrillated. This is accomplished by administering electrotherapy, such as a defibrillation shock. If a child ("pediatric") patient is sensed, then the defibrillation energy level may be adapted automatically (e.g. be set to 50 J). Such sensing may be from responder inputs, the belt or vest size when tightened around the patient, etc.

In some embodiments of the invention, at box 2030, instead of delivering a defibrillation shock, the CPR portion is used to deliver a precordial thump to deliver the patient. In particular, when the device detects a shockable rhythm, rather than delivering an electrical defibrillation pulse, the device first deliver a precordial thump to the patient, via the chest compression device, to attempt defibrillation. This is a great advantage of the invention, in that it can revert from one form of therapy to another.

In yet other embodiments, based on the patient's downtime (which could be entered into the device by the caregiver), or by analysis of parameter that indicates probability of shock success (such as ECG), it may first be decided whether to deliver electrotherapy, or to first perform CPR, and/or to first deliver medications prior to defibrillating. That action could either be started automatically by the system, or could be started with manual action from the user.

Execution may then return to box 2010, where inputs are received and analyzed. In a preferred optional embodiment, however, according to a next box 2040, Cardiopulmonary Resuscitation (CPR) is either performed automatically, or instructed for the responder to perform, after defibrillating. Instruction may be by voice commands, and/or may include sounds for the responder to synchronize their action. In addition, depending on the monitored inputs, the repetition rate of the CPR is adjusted. Further, if CPR is performed automatically, the force and its time profile are also adjusted. Execution returns to box 2010.

According to important alternate embodiments of the invention, boxes 2030 and 2040 take place together. In other words, defibrillation takes place while CPR is being performed automatically.

Referring briefly to FIG. 19, a time profile of the chest compressions is shown. More particularly, the changing circumference of the patient chest is plotted, as squeezed and released. In addition, the main level of the patient impedance is plotted in dashed lines, following in pattern the time profile of the chest circumference. (Other impedance variations may be superimposed on the main level of impedance). The profile of chest squeezing may be known directly, or indirectly from a monitored parameter such as the main level of impedance.

Advantageously, defibrillation (the large lightning bolts in FIG. 19) may take place any time in the CPR cycle. The exact timing is chosen in synchronization to pursue various optimizations. For example, if it is desired to exploit the smallest possible impedance, defibrillation happens according to bolt (A). On the other hand, if it is desired to exploit the moment that the heart is filled with the most blood (and thus draw the most current through the heart), then defibrillation happens according to bolt (B).

CPR may continue after defibrillation, or even be halted after it. An advantage of the invention is that the waiting time from CPR to defibrillation is minimized. Pacing takes place as described later in this document.

Returning to FIG. 18, if, at box 2020 it is determined that the patient is not undergoing VF, then according to an optional next box 2050, it is inquired whether a pulse is detected. If not, then according to an optional next box 2060, it is inquired whether the condition of Ventricular Tachycardia (VT) is detected. If so, then execution reverts to box 2030, and the patient is defibrillated. But if no VT is detected at box 2060, then execution reverts to box 2040 for performing CPR.

If a pulse is detected at box 2050, then, according to an optional next box 2070, it is inquired whether respiration is detected. If so, then execution returns to box 2010. Respiration may be detected automatically by respiration sensors, such as a $CO_2$ (carbon dioxide) sensor, chest movement sensor, or an impedance sensor.

If at box 2070 there is no respiration detected, then according to an optional next box 2080, ventilation is performed automatically by a ventilator, or rescue breathing is instructed for the responder to perform. Execution returns to box 2010.

Since box 2010 is preferably executed continuously, the method also includes discontinuing one type of therapy, and optionally also starting another consistently with the above. Also, if one of the signs changes, execution may return to box 2010 and start over. For example, pulse may be lost while ventilating. Or the onset of respiration may detected, in which case other activities (such as ventilation) stop.

Referring now to optional box 2090, optional pacing according to the invention is also described. In the embodiment of FIG. 18, the condition for enabling pacing is examined in two circumstances, namely in transitioning from box 2050 to 2070, and also in transitioning from box 2060 to 2040.

Figure 20:
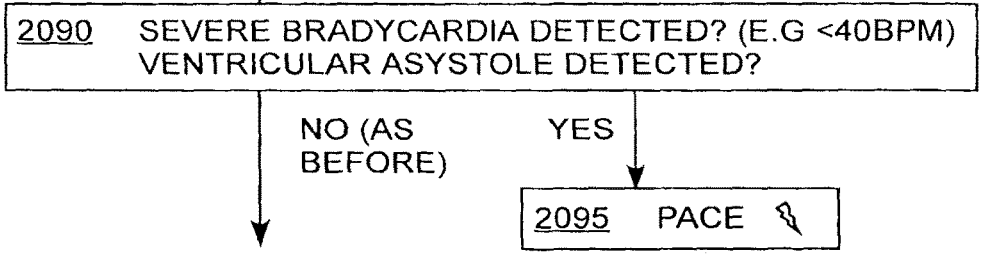
FIG. 20 is a flow chart segment illustrating an optional pacing portion of the flow chart of FIG. 18.

Referring now to FIG. 20, box 2090 is described in more detail. In both cases, it is inquired whether severe bradycardia is detected. In addition, if no pulse has been detected, it is inquired whether ventricular asystole has been detected. If not, then execution continues as before (from box 2050 to 2070, and from box 2060 to 2040). If yes, then according to a box 2095, pacing is performed.

Returning to FIG. 19, pacing (shown as a small lightning bolt) may also be coordinated with the administration of CPR. Pacing is preferably synchronized with the compression cycle. There is some evidence that chest compressions may cause a QRS complex (ventricular depolarization), if the heart is able to support it. Accordingly, pacing during the compression cycle provides the additional impetus to the ventricles. Also, pacing should be avoided a few 100 msec after a QRS complex, during the ventricular vulnerability period.

At any one time during the method of FIG. 18, inputs are received (for monitoring) from the available sensors, and from the user through the I/O module. Outputs are communicated to the user through the I/O module.

Figure 21:
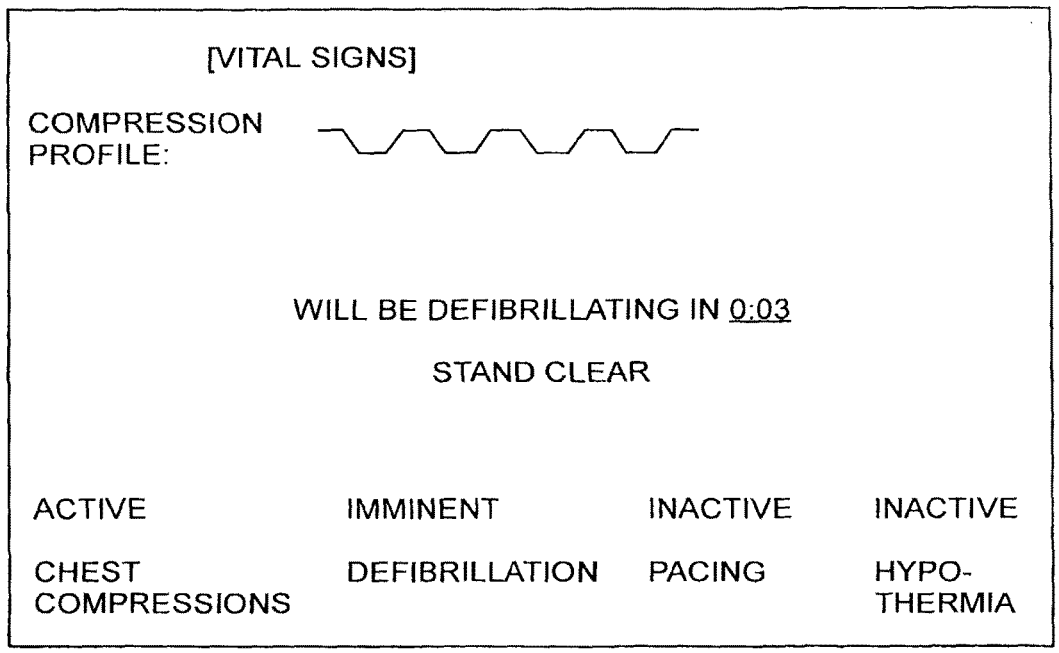
FIG. 21 is a view of a display screen from an operation of the invention.

Referring now to FIG. 21, a sample screen snapshot is shown. The screen is advantageously used for communicating to the user the monitored data (such as vital signs), outputs, comments, actions, etc. In the example of FIG. 21, there is a count down for imminent defibrillation (at the 3 sec point).

A person skilled in the art will be able to practice the present invention in view of the description present in this document, which is to be taken as a whole. Numerous details have been set forth in order to provide a more thorough understanding of the invention. In other instances, well-known features have not been described in detail in order not to obscure unnecessarily the invention.

While the invention has been disclosed in its preferred form, the specific embodiments as disclosed and illustrated herein are not to be considered in a limiting sense. Indeed, it should be readily apparent to those skilled in the art in view of the present description that the invention may be modified in numerous ways. The inventors regard the subject matter of the invention to include all combinations and subcombinations of the various elements, features, functions and/or properties disclosed herein.

What is claimed is:

1. A device for performing external chest compression (ECC) on a person, the device comprising:
   a backboard structured to support the person thereon and to extend across a posterior portion of the person;
   at least one chest compression member integrated within and rigidly connected to at least one of two rigid arms configured to extend across an anterior portion of a chest of the person, the two rigid arms also attached to the backboard at respective first ends, the combination of the backboard and the two rigid arms surrounding the person's chest, the chest compression member configured to deliver chest compressions to the person by pushing down on the anterior portion of the person's chest while the posterior portion of the person's chest remains stationary against the backboard; and
   at least one wheel attached to the backboard, the wheel structured to facilitate movement of the backboard along a surface while the person is supported on the backboard.

2. A device as in claim 1, further comprising:
   a defibrillator module coupled to the backboard and structured to administer defibrillation therapy to the person.

3. A device as in claim 2, further comprising:
   at least one sensor structured to sense physiological data from the person and structured to transmit the sensed physiological data to the defibrillator module.

4. A device as in claim 3, in which the physiological data includes at least one attribute from the group consisting of pulse, ECG, heartbeat, breathing, body temperature, externally applied chest pressure and thoracic impedance.

5. A device as in claim 3, further comprising a controller coupled to the at least one sensor and configured to execute logic to defibrillate the person responsive to sensor data indicative of cardiac arrest.

6. A device as in claim 3, further comprising a pacing module and a controller coupled to the at least one sensor and configured to execute logic to pace the person responsive to sensor data indicative of Bradycardia.

7. A device as in claim 3, wherein one or more of the sensors are integrated into the chest compression member.

8. A device as in claim 2, wherein the defibrillator module includes defibrillation electrodes integrated into the chest compression member.

9. A device as in claim 2, wherein the defibrillator module includes defibrillation electrodes including a releasable electrolyte.

10. A device as in claim 1, further comprising:
    a cooling module configured to cool the person;
    at least one sensor; and
    a controller coupled to the at least one sensor and configured to execute logic to initiate cooling using the cooling module responsive to sensor data indicative of at least one of a group consisting of:
    cardiac arrest in the person;
    stroke in the person; and
    acute myocardial infarction in the person.

11. A device as in claim 1, further comprising:
    a ventilator coupled to the backboard;
    at least one respiration sensor; and
    a controller coupled to the at least one sensor and configured to execute logic to initiate ventilating the person using the ventilator responsive to sensor data indicative of lack of respiration in the person.

12. A method comprising:
    providing a backboard of a device, the backboard configured to have a person placed on the backboard, wherein the device includes:
    the backboard structured to support the person thereon and to extend across a posterior portion of the person;
    at least one chest compression member integrated within and rigidly connected to at least one of two rigid arms configured to extend across an anterior portion of a chest of the person, the two rigid arms also attached to the backboard at respective first ends, the combination of the backboard and the two rigid arms surrounding the person's chest, the chest compression member configured to deliver chest compressions to the person by pushing down on the anterior portion of the person's chest while the posterior portion of the person's chest remains stationary against the backboard; and
    at least one wheel attached to the backboard, the wheel structured to facilitate movement of the backboard along a surface while the person is supported on the backboard;
    causing the chest compression member of the device to compress a chest of the person against the backboard; and
    causing the person to move by rolling the backboard along the ground via the at least one wheel.

13. The method of claim 12, wherein the device includes at least one sensor and a defibrillation module, the method further comprising:
    causing the device to sense physiological signals of the person with the sensor; and
    causing the defibrillation module of the device to defibrillate the person responsive to the signals.

14. The method of claim 13, in which the physiological data includes at least one attribute from the group consisting of pulse, ECG, heartbeat, breathing, body temperature, externally applied chest pressure and thoracic impedance.

15. The method of claim 12, further comprising generating a voice output of the device and outputting the voice output from the device.

16. The method of claim 12, wherein the device includes at least one sensor and a cooling module, the method further comprising:
    causing the device to sense physiological signals of the person with the sensor; and
    causing the cooling module of the device to initiate cooling of the person responsive to the signals.

17. The method of claim 12, wherein the device includes at least one sensor and a ventilator, the method further comprising:
    causing the device to measure respiration in the person with the sensor; and
    causing the ventilator of the device to initiate ventilation of the person responsive to the measured respiration.

18. A chest compression device, comprising:
    a backboard;
    a pair of rigid arms each coupled to the backboard at respective first ends;

a chest compressor supported by at least one of the pair of rigid arms in a position above the backboard, the chest compressor rigidly connected to the at least one of the pair of rigid arms and structured to administer chest compressions to a patient; and a communications module electrically coupled to the chest compression device and configured to at least one of transmit and receive data that includes at least one of operation of the chest compression device and patient physiological data.

19. The chest compression device of claim 18, wherein at least one of the pair of rigid arms is pivotably coupled to the backboard at its respective first end.

20. The chest compression device of claim 18, wherein the chest compressor is integrated with at least one of the pair of rigid arms.

21. The chest compression device of claim 18, further comprising a sensor configured to sense at least one patient physiological data, the sensor electrically coupled to the communications module and configured to output the at least one patient physiological data to the communications module.

22. The chest compression device of claim 21, wherein the sensor is integrated within one of the backboard, the pair of rigid arms, and the chest compressor.

23. The chest compression device of claim 18, wherein the communications module is configured to transmit data to and receive data from a network.

24. The chest compression device of claim 23, wherein the communications module is further configured to receive a command code that includes an instruction for operating the chest compression device.

25. The chest compression device of claim 18, further comprising a defibrillating module having an electrode that is electrically coupled to one of the backboard and the chest compressor and configured to administer defibrillating therapy to the patient.

26. The chest compression device of claim 25, wherein the defibrillating module is further configured to administer pacing to the patient.

27. The chest compression device of claim 25, wherein the defibrillating module is integrated within one of the backboard or the chest compressor.

28. The chest compression device of claim 18, wherein the chest compressor is further structured to administer abdominal compressions to the patient.

29. The chest compression device of claim 18, wherein the chest compressor is structured to administer compression-decompression to the patient.

30. A chest compression device, comprising:

a pair of rigid arms;

a chest compressor supported by at least one of the pair of rigid arms in a position above a chest of a patient, the chest compressor rigidly connected to the at least one of the pair of rigid arms and structured to administer chest compressions to the patient;

a sensor integrated in one of the pair of rigid arms and the chest compressor, the sensor configured to sense at least one of operation of the chest compression device and patient physiological data; and a communications module electrically coupled to the sensor and configured to at least one of transmit and receive the data sensed by the sensor that includes at least one of the operation of the chest compression device and the patient physiological data.

31. The chest compression device of claim 30, wherein at least one of the pair of rigid arms is structured to be pivotably attached to a backboard at its first end.

32. The chest compression device of claim 30, wherein the chest compressor is integrated with at least one of the pair of rigid arms.

33. The chest compression device of claim 30, wherein the communications module is configured to transmit data to and receive data from a network.

34. The chest compression device of claim 33, wherein the communications module is configured to receive a command code that includes an instruction for operating the chest compression device.

35. The chest compression device of claim 34, wherein the command code includes a signal for the chest compressor to administer one of chest compressions, defibrillation, and pacing to the patient.

36. The chest compression device of claim 30, wherein the chest compressor is further structured to administer at least one of defibrillation, abdominal compressions, and pacing to the patient.

37. The chest compression device of claim 30, the chest compressor is structured to administer compression-decompression to the patient.

* * * * *